(12) United States Patent
Chen et al.

(10) Patent No.: US 8,248,585 B2
(45) Date of Patent: Aug. 21, 2012

(54) LASER CAPTURE MICRODISSECTION SYSTEM AND ELECTRIC MOVING STAGE THEREOF

(76) Inventors: Chien-Ming Chen, Taipei (TW); Jen-Ai Lee, Taipei (TW)

( * ) Notice: Subject to any disclaimer, the term of this patent is extended or adjusted under 35 U.S.C. 154(b) by 306 days.

(21) Appl. No.: 12/654,330

(22) Filed: Dec. 17, 2009

(65) Prior Publication Data
US 2010/0157284 A1 Jun. 24, 2010

(30) Foreign Application Priority Data

Dec. 22, 2008 (TW) .............................. 97150136 A

(51) Int. Cl.
*G01N 1/00* (2006.01)

(52) U.S. Cl. ........................................................ 356/36

(58) Field of Classification Search ..................... 356/36; 385/33; 435/4, 283.1, 808
See application file for complete search history.

(56) References Cited

U.S. PATENT DOCUMENTS

| | | | | |
|---|---|---|---|---|
| 5,286,970 A * | 2/1994 | Betzig et al. | ............. | 250/227.26 |
| 5,859,699 A * | 1/1999 | Baer et al. | ..................... | 356/246 |
| 6,420,132 B1 * | 7/2002 | Bonner et al. | ............... | 435/40.5 |
| 6,469,779 B2 * | 10/2002 | Baer et al. | ....................... | 356/36 |
| 7,968,819 B2 * | 6/2011 | Okada | ...................... | 219/121.67 |
| 2010/0120113 A1 * | 5/2010 | Mohanty et al. | ........... | 435/173.1 |

* cited by examiner

*Primary Examiner* — Layla Lauchman
(74) *Attorney, Agent, or Firm* — Bacon & Thomas, PLLC

(57) ABSTRACT

A laser capture microdissection system includes a laser illuminator, a fiber and an electric moving stage. The fiber has a probe terminal and a coupling terminal for being coupled to the laser illuminator. The electric moving stage includes a fiber probe holder, a driving mechanism for vertical shift, a stage unit, a driving mechanism for horizontal shift and an electronic control unit. The driving mechanism for vertical shift serves for driving the fiber probe holder to shift in microscale. The stage unit has a nanoscale shift controller, a placing portion, wherein the nano-scale shift controller is connected to the placing portion, and the placing portion is located under the fiber probe holder. The driving mechanism for horizontal shift serves for driving the stage unit to shift in microscale. The electronic control unit is electrically connected to the nanoscale shift controller and the driving mechanism for horizontal shift.

19 Claims, 10 Drawing Sheets

LASER CAPTURE MICRODISSECTION SYSTEM AND ELECTRIC MOVING STAGE THEREOF

BACKGROUND OF THE INVENTION (1) Field of the Invention

The invention relates to a laser capture microdissection system and an electric moving stage thereof, especially relates a laser capture microdissection system and an electric moving stage thereof for serving to capture the nanoscale particles or biological samples, such as the nanoscale tissue cell.

(2) Description of the Prior Art

Following the advancement and accumulation of the optoelectronics knowledge as well as the progress in the optoelectronics technology, engineers and scientists are urged to exploit and employ the laser technology together with precise electric position control into nanoscale so that an user-friendly simple opto-electric positioning mechanism can be worked out for capture, separation or dissection of the target cell specimen via laser technology in simple, quick and precise manner.

Currently, laser systems for capture, separation or dissection of the target cell specimen can be roughly categorized into three generations chronologically: 1. Primeval Laser Capture Microdissection (LCM); 2. Laser Microdissection and Pressure Catapulting (LMPC); and 3. Leica AS LMD. Wherein, the first generation Laser Capture Microdissection (LCM) is still most popularly adopted for following reasons: well known due to earliest development; comprehensive existing information and documents accumulated about sample preparation from experienced users; low price relatively; and easy and quick operation in dissection process.

Refer to FIG. 1 for the schematic view showing the structural configuration of a conventional laser capture microdissection system 100. The conventional laser capture microdissection system 100 mainly includes an inverted microscope 110, a laser diode 120, a fiber probe 130, an ethylene vinyl acetate (EVA) transfer membrane 140 and a glass slide 150. The inverted microscope 110 has a microscopic stage and an objective. The practical operation is described as below: Firstly, attach the EVA transfer membrane 140 over a histological tissue slice 200, then place the tissue slice 200 on the microscopic stage of the inverted microscope 110 for being observed by the suitable objective; Secondly, shift the tissue slice 200 to identify target cells (not shown) of interest in a target area of the microscope field; Thirdly, set up the laser diode 120 and the fiber probe 130 at suitable locations so that a laser beam, which is illuminated from the laser diode 120 with high optical energy density formed via the fiber probe 130, irradiates the EVA transfer membrane 140 over the target cells of interest to form a light spot 142; Fourthly, the EVA transfer membrane 140, which is heated up to its melting point via absorption the optical energy of the irradiated laser beam from the laser diode 120, becomes strong adhesive and enabled to bind the target cells of interest.

Finally, tear the EVA transfer membrane 140 away from the tissue slice 200. Because the melted adhesive binding force between the target cells and the EVA transfer membrane 140 is greater than the attaching force between the target cells and the peripheral tissue, the target cells with the EVA transfer membrane 140 is sliced from the tissue slice 200 to get apart.

However, the size of most plant cells is between 100 to 200 micrometer, and the size of the animal cell is about one-tenth of the size of the plant cell. For getting the captured result better, the diameter of the target cell is at least lager than or equal 5 micrometer. When the diameter of the target cell is smaller than 5 micrometer, the captured parts of cell inevitably contain the tissue close to the target cell, probably contaminating the target cell.

Refer to FIG. 2, for the schematic view showing a stage 250 of a conventional laser capture microdissection system 100. The conventional stage 250 provides a place for laying the glass slide 150, the EVA transfer membrane 140 and the tissue slice 200 thereon. During dissecting process, the target cells should be centered in a target area of the microscope field (dashed circle) for being inspected the light spot 142, which appears on the EVA transfer membrane 140 irradiated by a low power laser beam from the laser diode 120 through fiber probe 130 in the inverted microscope 110.

However, because of no fine tuning feature for precise movement of the conventional stage 250, the alignment of the fiber probe 130 with the target cells is a very difficult and hours time-consuming task so that the overall microdissection process becomes very slow.

SUMMARY OF THE INVENTION

Accordingly, the object of the invention is to provide an electric moving stage for a laser capture microdissection system. After capturing the target object via the image observed by the charge coupled device (CCD) camera, the operation and the control of the man-machine interface is accomplished effectively to promote the overall speed of the laser capture microdissection (LCM) system.

In one aspect, the invention provides a laser capture microdissection system including a shift control unit, an optical unit and an electronic control unit electrically connected to the shift control unit. The optical unit includes a laser illuminator and a fiber. The laser illuminator is electrically connected to the electronic control unit for switching a triggered time of the laser illuminator wherein the triggered time is larger than 30 millisecond, and the fiber is coupled to the laser illuminator and has a probe terminal fixed on the shift control unit. An aperture of the probe terminal is smaller than 200 nanometer. Wherein a surface of the probe terminal of the fiber is plated with a gold film or a silver film, whose thickness is 10 to 99 nanometer.

The laser capture microdissection system further includes a transfer membrane disposed under the probe terminal of the fiber.

The shift control unit further includes a first piezoelectric (PZT) actuator, a second PZT actuator and an adapted gasket, and the first PZT actuator and the second PZT actuator are combined by the adapted gasket. Wherein the first PZT actuator has a first fixed end and a first moving end shifted with a first axis corresponding to the first fixed end. The second PZT actuator has a second fixed end and a second moving end shifted with a second axis corresponding to the second fixed end. The second fixed end of the second PZT actuator is fixed on the first moving end of the first PZT actuator, and the probe terminal of the fiber is fixed on the second moving end of the second PZT actuator. The shift control unit further includes a shift stage for three axis, and the first fixed end of the first PZT actuator is fixed on the shift stage for three axis.

In another aspect, the invention provides a laser capture microdissection system including a laser illuminator, a fiber and an electric moving stage. The fiber has a probe terminal and a coupling terminal. The coupling terminal is coupled to the laser illuminator and inserts in holder aperture of the fiber probe holder of the electric moving stag. The electric moving stage includes a stage unit, a driving mechanism for horizontal shift, a driving mechanism for vertical shift, a fiber probe holder and an electronic control unit. The stage unit is disposed on the substrate and has a nanoscale shift controller, a placing portion and a hollow portion. The placing portion is inside the hollow portion. The nanoscale controller is connected to the placing portion. The driving mechanism for horizontal shift is disposed on the substrate for driving the stage unit to shift in micro-scale. The driving mechanism for vertical shift is disposed on the substrate for driving the fiber probe holder to shift in micro-scale. The fiber probe holder provides a holder aperture located on the placing portion of the stage unit. The electronic control unit is electrically connected to the nanoscale shift controller and the driving mechanism for horizontal shift.

The nanoscale shift controller of the stage unit is a PZT actuator for controlling the displacement of the placing portion in nanoscale. The hollow portion of the stage unit is a rectangular pit for accommodating a glass slide to be supported by the placing portion.

The driving mechanism for horizontal shift includes a stepping motor and a ball screw shaft so that the stage unit is motorized by the ball screw shaft driven by the stepping motor.

The driving mechanism for vertical shift includes a PZT actuator for controlling the displacement of the holder aperture of the fiber probe holder in nanoscale. The driving mechanism for vertical shift has a manual rotary shaft.

The electronic control unit includes a stepping motor driver, a PZT actuator driver and a personal computer (PC), the stepping motor driver electrically connects to the driving mechanism for horizontal shift, and the
PZT actuator driver electrically connects to the nanoscale shift controller and the driving mechanism for vertical shift.

In still another aspect, the invention provides an electric moving stage for a laser capture microdissection system includes a substrate, and said stage unit, said driving mechanism for horizontal shift, said driving mechanism for vertical shift, said fiber probe holder and said electronic control unit.

The movement of the stage unit and the movement of the fiber probe in the present invention are separated and independent of each other. The movement of the fiber probe is shifted in three-dimensional (X, Y and Z axis) direction. Whereas, the movement of the stage unit is relatively confined in planar two-dimensional (X and Y axis) direction. The overall speed and performance of the LCM system is enable be significantly improved via the man-machine interface.

BRIEF DESCRIPTION OF THE DRAWINGS

The present invention will now be specified with reference to its preferred embodiment illustrated in the drawings, in which.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. In this regard, directional terminology, such as "top," "bottom," "front," "back," etc., is used with reference to the orientation of the Figure(s) being described. The components of the present invention can be positioned in a number of different orientations. As such, the directional terminology is used for purposes of illustration and is in no way limiting. On the other hand, the drawings are only schematic and the sizes of components may be exaggerated for clarity. It is to be understood that other embodiments may be utilized and structural changes may be made without departing from the scope of the present invention. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. Similarly, the terms "facing," "faces" and variations thereof herein are used broadly and encompass direct and indirect facing, and "adjacent to" and variations thereof herein are used broadly and encompass directly and indirectly "adjacent to". Therefore, the description of "A" component facing "B" component herein may contain the situations that "A" component facing "B" component directly or one or more additional components is between "A" component and "B" component. Also, the description of "A" component "adjacent to" "B" component herein may contain the situations that "A" component is directly "adjacent to" "B" component or one or more additional components is between "A" component and "B" component. Accordingly, the drawings and descriptions will be regarded as illustrative in nature and not as restrictive.

Figure 1:
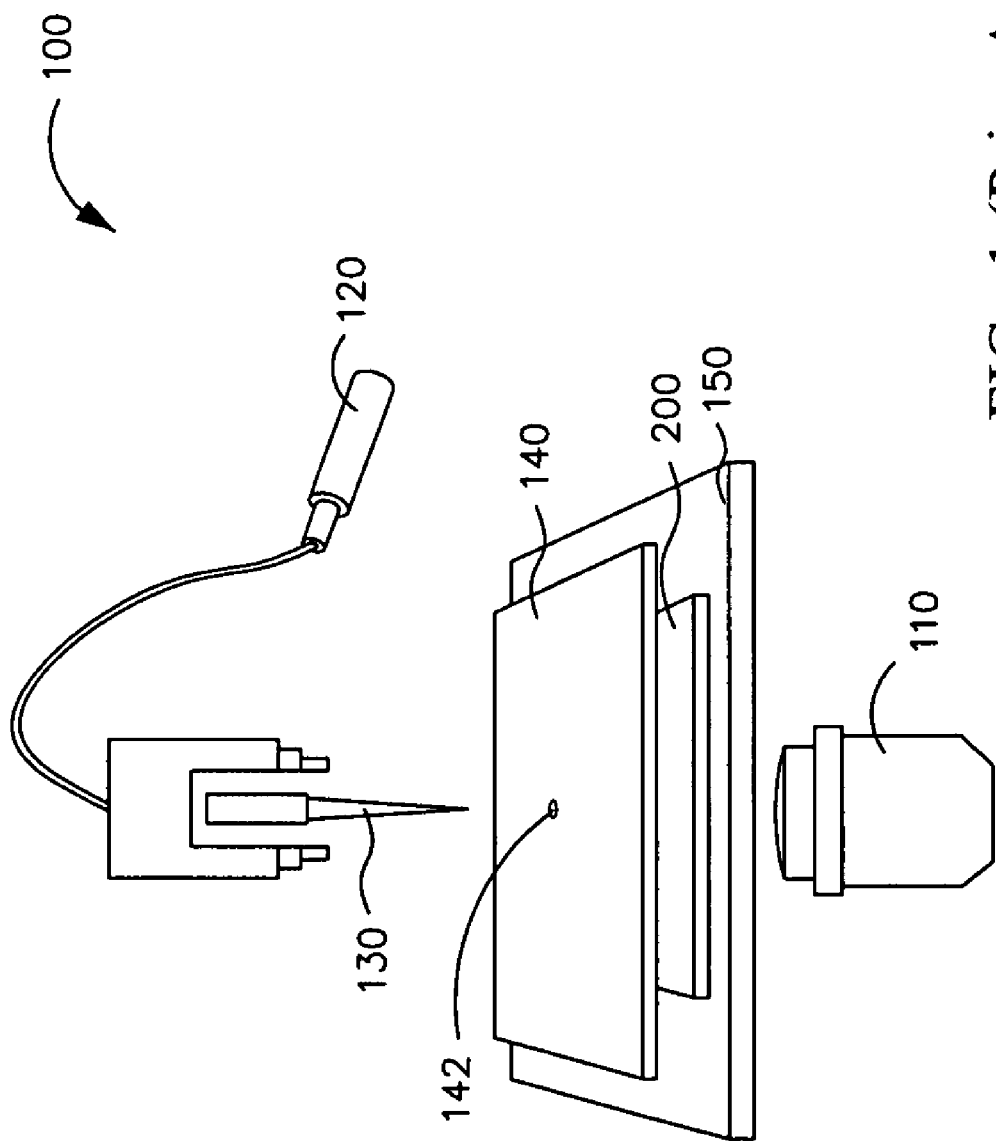
FIG. 1 is a schematic view showing the structural configuration of a conventional laser capture microdissection system.
Figure 2:
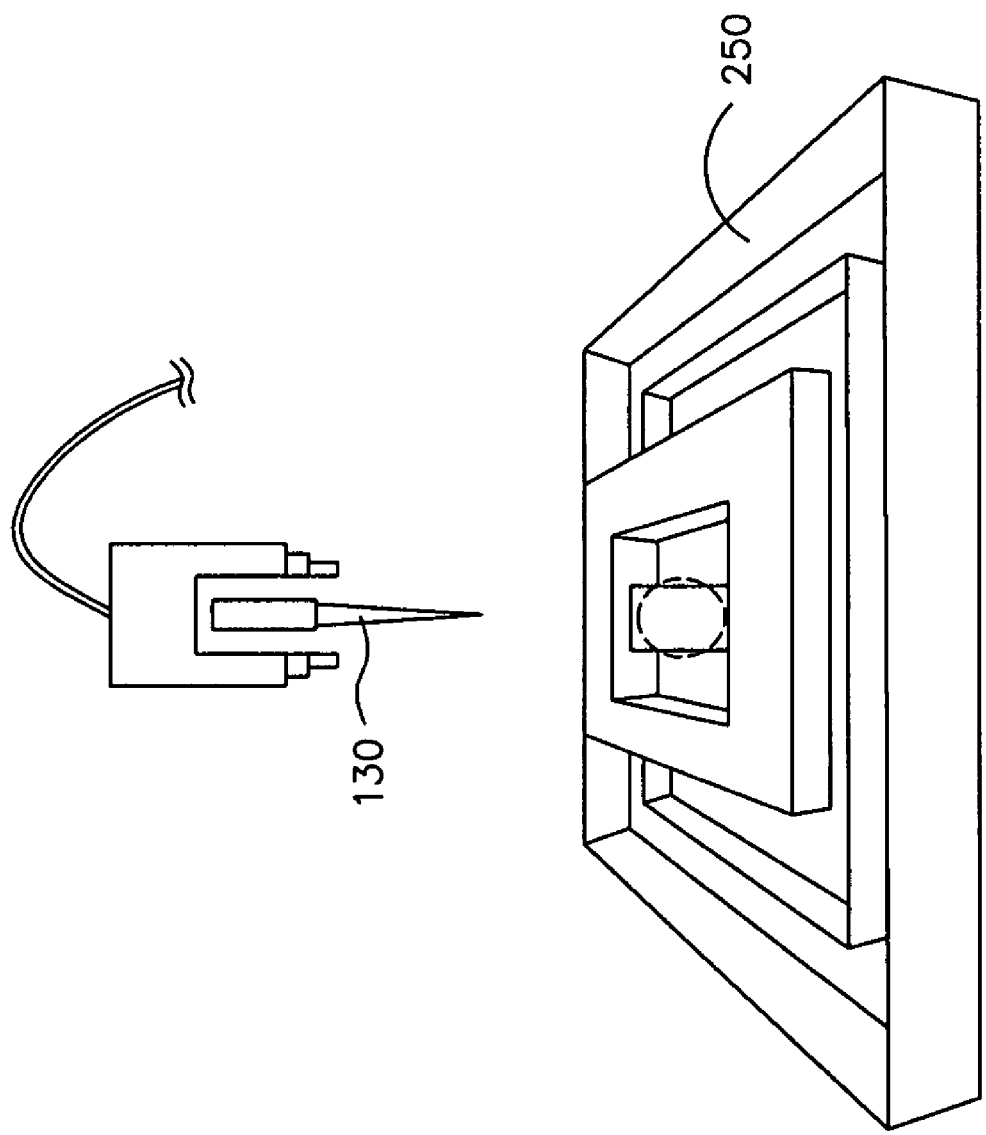
FIG. 2 is a schematic view showing the structural configuration for a stage unit of a conventional laser capture microdissection system.
Figure 3:
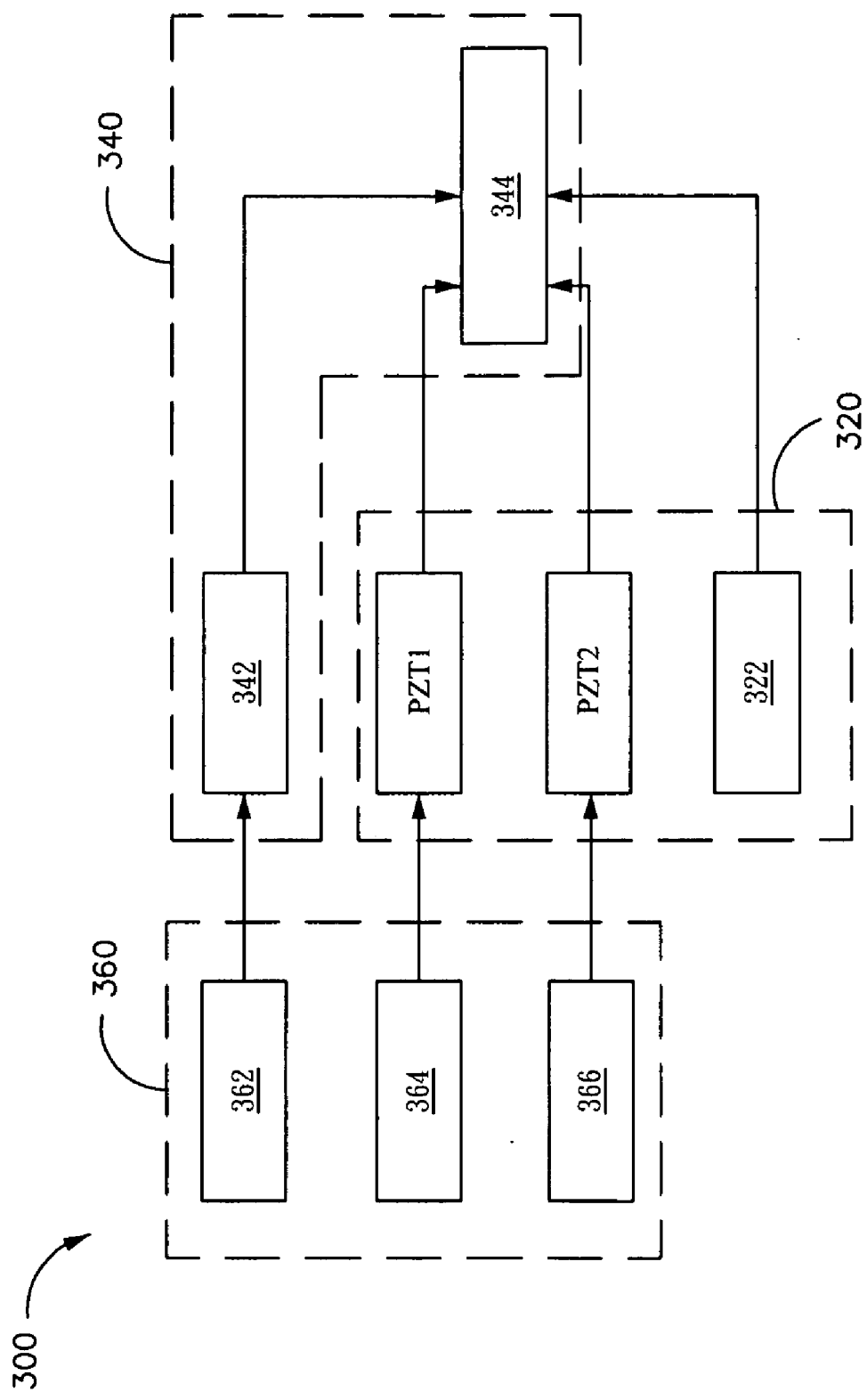
FIG.3 is a block diagram showing a control function of a shift control unit, an optical unit and an electronic control unit for a laser capture microdissection system of the present invention.

Refer to FIG. 3, a laser capture microdissection system 300 includes a shift control unit 320, an optical unit 340 and an electronic control unit 360. The components combined to form the shift control unit 320 include two piezoelectric actuators PZT1 and PZT2 and a shift stage for three axis 322. The components combined to form the optical unit 340 include a laser illuminator and a fiber 344. The laser illuminator is a laser diode 342, and the fiber 344 includes a probe terminal. The components combined to form the electronic control unit 360 include a laser diode driving circuit 362 and two drivers 364 and 366, respectively adapted to drive the piezoelectric actuators PZT1 and PZT2.

The control function of every component in the laser capture microdissection system 300 is recited as below. Two drivers 364 and 366 respectively provide two driving voltages for two piezoelectric actuators PZT1 and PZT2 separately controlling the probe terminal of the fiber 344 stirring in Z-axis and X-axis. The shift stage for three axis 322 takes charge to orientate with long distance in X,Y,Z-axis. The laser diode driving circuit 362 provides a driving current for the laser diode 342 switching the triggered time. In an example, the triggered time is from 0 to 9999 millisecond, preferably, larger than 30 millisecond.

Figure 4A:
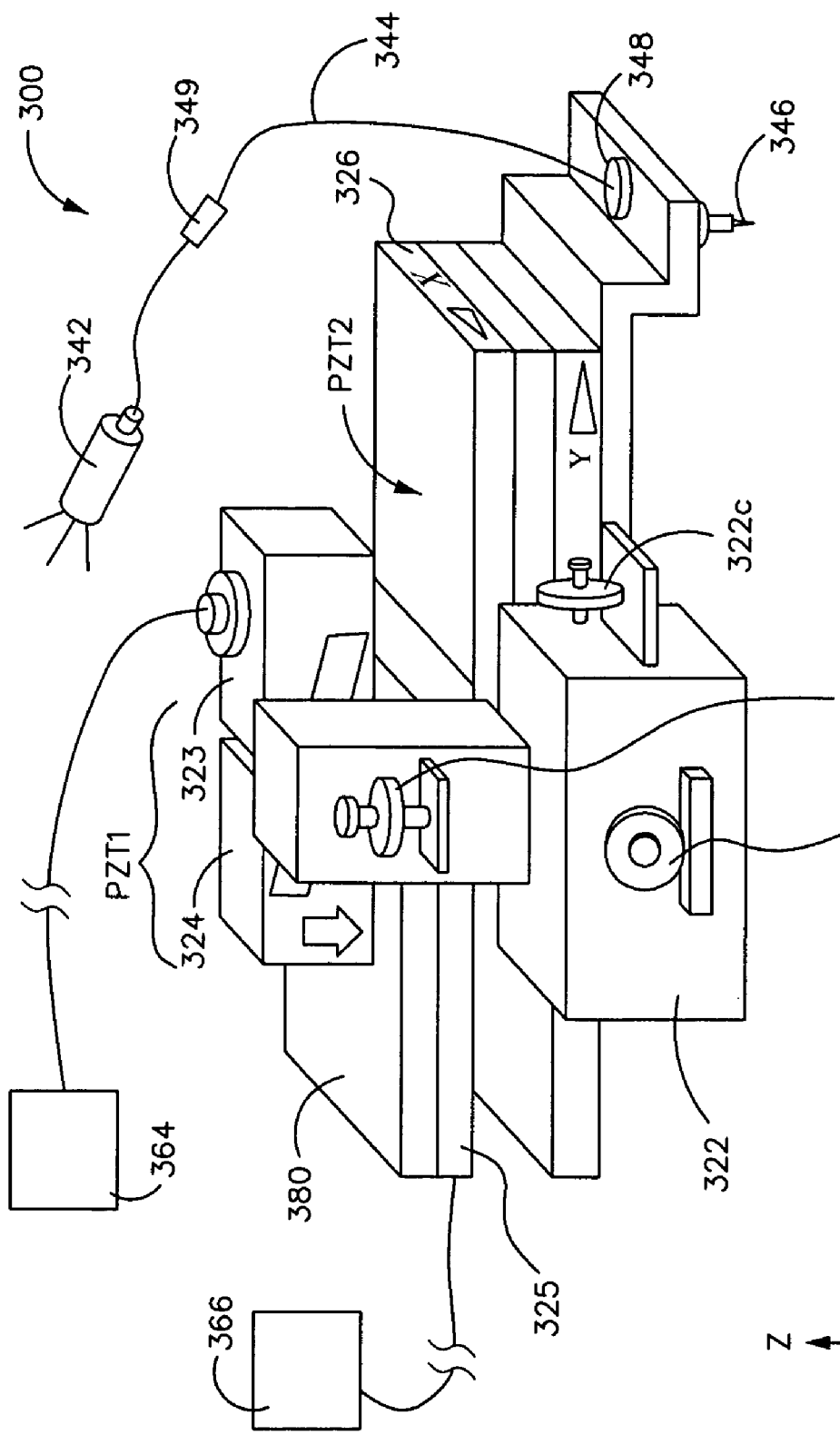
FIG. 4A and FIG. 4B are schematic views showing the structural configuration for a laser capture microdissection system.
Figure 4B:
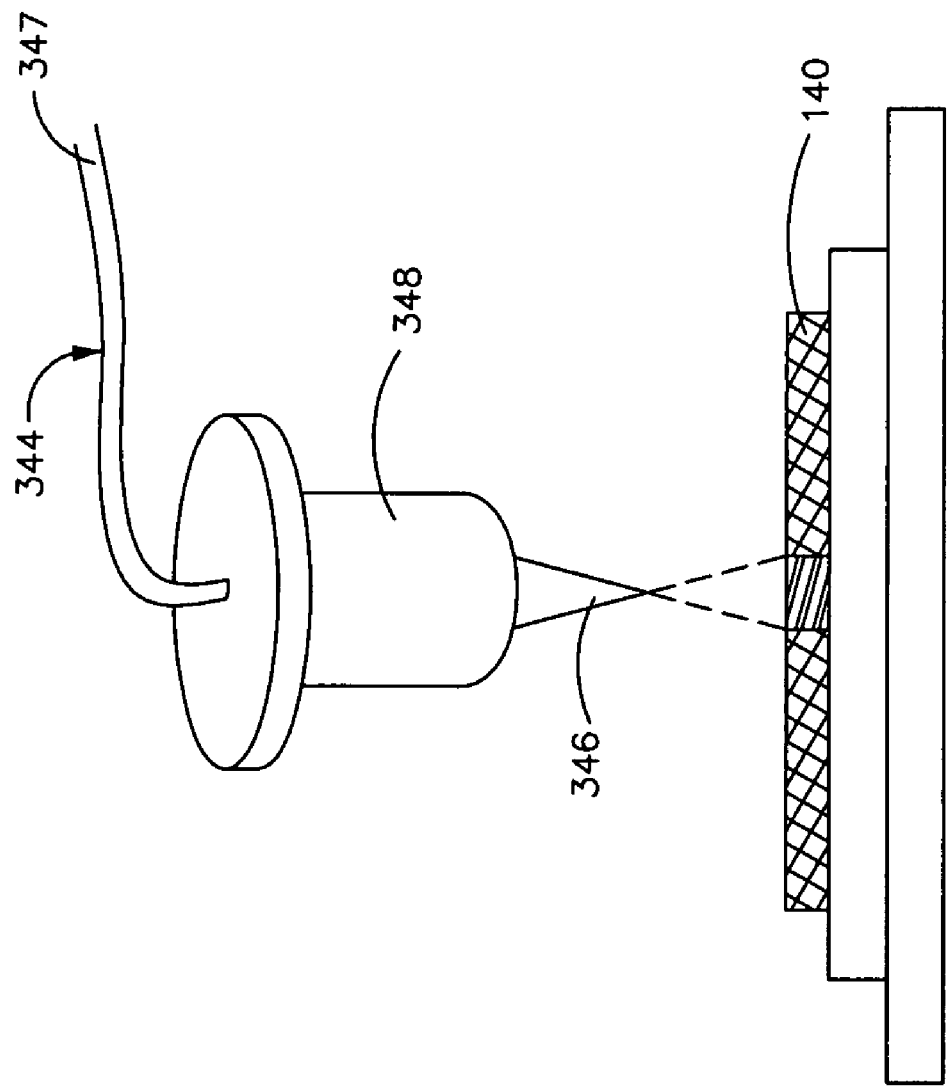

Refer to FIG. 4A and FIG. 4B for schematic views showing the structural configuration for the laser capture microdissection system 300. The laser capture microdissection system 300 is composed of eight components, and the functions are recited as below.

1. Piezoelectric actuator PZT1: The piezoelectric actuator PZT1 has a fixed end 323 and a moving end 324. The fixed end 323 is fixed on the shift stage for three axis 322. The moving end 324 corresponding to the fixed end 323 is shifted with relative displacement of 0~30 μm in Z-axis to response input voltage range of 0~−1000 V.

2. Piezoelectric actuator PZT2: The piezoelectric actuator PZT2 has a fixed end 325 and a moving end 326. The moving end 326 corresponding to the fixed end 325 is shifted with relative displacement of 0~65 μm in X-axis to response input voltage range of −10~−150 V. The fixed end 325 is fixed on the moving end 324 of the piezoelectric actuator PZT1 by an adapted gasket 380.

3. Shift stage for three axis 322: The shift stage for three axis 322 is controlled by three manual rotary shafts 322a, 322b, and 322c. The shift stage for three axis 322 is moved with the displacement of 10 μm by turning per step of the thread spacing. Each manual rotary shaft is carved up to 600 steps, and the range of the readable displacement is 6 mm in X,Y and Z-axis direction. The actuation principle of the manual rotary shaft is used by turning per thread spacing, so the problem of backlash error is easy to be generated.

4. Fiber 344: Refer to FIG. 4B in the meanwhile, the fiber 344 has a probe terminal 346 and a coupling terminal 347. The probe terminal 346 is fastened by a fiber probe holder 348 and fixed on the moving end 326 of the piezoelectric actuator PZT2 with the fiber probe holder 348. The laser illuminator is input by the coupling terminal 347 of the fiber 344 such as a SC adapter.

5. Laser diode 342: The fiber 344 in the embodiment is a single mode fiber (SMF). Because the laser is coupled in the fiber 344 and the power loss of the laser beam focused by the fiber 344 is quite great (loss>99%), the laser diode 342 is chosen as well as high-power and the package of the laser diode 342 is a pigtail.

In another embodiment, after the laser is coupled in the single mode fiber by a micro lens, the laser diode 342 is packaged to form the pigtail by laser welding and the output is the SC adapter 349. The laser diode is used with no cap for processing simplification.

6. Driver 364 of the piezoelectric actuator PZT1: The driver 364 is output voltage by a knob. The knob is carved up to 100 steps of the thread spacing representing the output of 0~−1000V, and the output voltage is changed with the output voltage of 10V by turning per step of the thread spacing.

7. Driver 366 of the piezoelectric actuator PZT2: The driver 366 is output voltage by a knob, and the voltage of −10~150V is displayed by a 3-digit seven segment display. The driver 366 outputs totally three sets of single voltages, and just one set of single voltage is used in the embodiment.

8. Laser diode driving circuit 362: Use a manual switch to control a laser triggered time with the range of 0 ms~9999 ms, and the laser diode driving circuit 362 provide the constant current of 0.3 A to the laser diode 342 according with the set laser triggered time.

Above all, the shift control unit 320 is adapted to orient the probe terminal 346 of the fiber 344 with precision. The piezoelectric actuators PZT1 and PZT2 are combined to form a precise positioning system with two axis by the adapted gasket 380, and respectively control the probe terminal 346 of the fiber 344 moving with tiny displacement in Z-axis and X-axis. The fiber probe holder 348 of the probe terminal 346 is fixed on the moving end 326 of the piezoelectric actuator PZT2, and able to shift with tiny right or left displacement in X-axis corresponding with the fixed end 325 of the piezoelectric actuator PZT2. Otherwise, the fixed end 325 of the piezoelectric actuator PZT2 is tightly fastened on the moving end 324 of the piezoelectric actuator PZT1, so the moving end 324 of the piezoelectric actuator PZT1 drives both the piezoelectric actuator PZT2 and the probe terminal 346 of the fiber 344 to move with the tiny displacement in Z-axis direction to response variable voltage input into the piezoelectric actuator PZT1.

The shift stage for three axis 322 is adapted to move quickly with large-scale displacement. The fixed end 323 of the piezoelectric actuator PZT1 is fixed on the shift stage for three axis 322 and adapted to control the piezoelectric actuators PZT1 and PZT2 and roughly orient the probe terminal 346 of the fiber 344.

Refer to 4B in the meanwhile, the most important ultimate principle of laser capture microdissection is using high density energy focused by the laser beam to heat and melt an EVA transfer membrane 140. The optical unit 340 of the embodiment is used to be the focusing component by the probe terminal 346 of the fiber 344. In an example, the distance between the probe terminal 346 and the EVA transfer membrane 140 is less than 1.3 micrometer. And the EVA transfer membrane 140 can be placed on a cannular carrier (not shown).

In order that the size of light spot on the EVA transfer membrane 140 approaches the size of a tiny aperture on the probe terminal 346 of the fiber 344 after the laser beam is focused by the probe terminal 346 of the fiber 344, and the power of the light spot is enable to melt the EVA transfer membrane 140, the distance between the probe terminal 346 and the EVA transfer membrane 140 is better to get shorter. However, the main material of the probe terminal 346 is fragile glass and the probe terminal 346 is etched as cone in nano-size, so the probe terminal 346 is fine and fragile. The probe terminal 346 is easy to be fractured if collided with the EVA transfer membrane 140. For solving above questions, setting the shift control unit 320 is necessary.

When unsealed to form the pigtail, the laser diode 342 outputs the power of 180 mW; when sealed, the laser diode 342 outputs the power of 10.21 mW, which is 5.672% of the power output by the laser diode 342 when unsealed, and the coupling terminal 347 is measured by an optical power meter.

For avoiding the low power of the laser illuminating the EVA transfer membrane 140, the present embodiment chooses the aperture of the probe terminal 346 of the fiber 344 is 150 nanometer, and the transmittance of the EVA transfer membrane 140 is about 0.854% to 1.372%, measured by the laser with wavelength of 633 nm.

The fiber 344, the probe terminal 346 and the coupling terminal 347 thereof are called an "optical fiber probe" as below. The optical fiber probe is processed by an usual single mode fiber, and the probe terminal 346 thereof is a conical pinpoint. The pinpoint has a tiny aperture, providing for the laser illuminating via, and being from 10 to 999 nm, or smaller than 200 nm, preferably 150 nm. The general scanning probe microscopy technique applied on a photon scanning tunneling microscope (PSTM) or other is the main tech of a scanning near-field optical microscope (SNOM).

Figure 5:
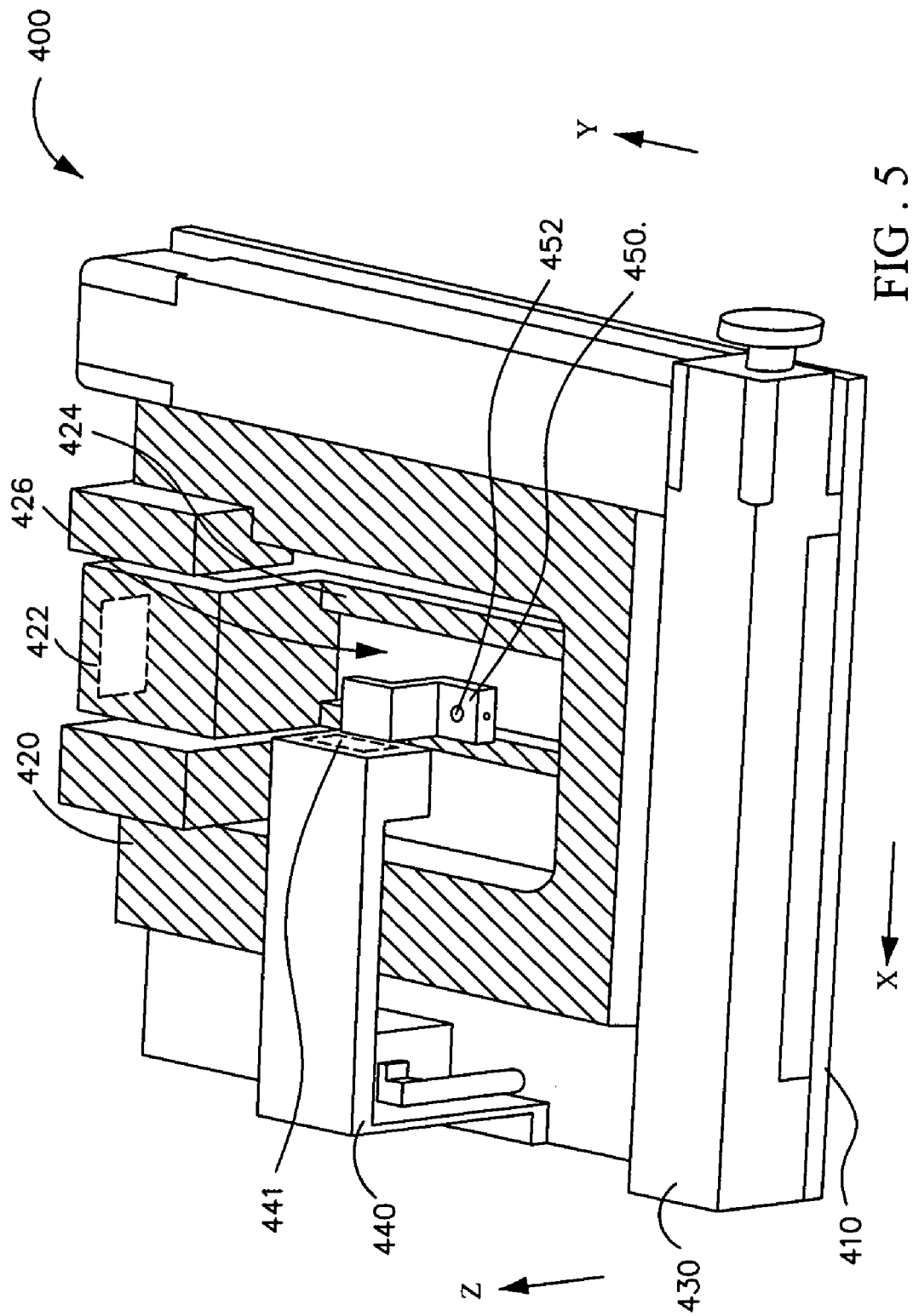
FIG. 5 is a schematic view showing an electric moving stage for a laser capture microdissection system of the present invention.

Refer to FIG. 5 for the schematic view showing an electric moving stage 400 for a laser capture microdissection(LCM) system of the present invention. The electric moving stage 400 includes a substrate 410, a stage unit 420, a driving mechanism for horizontal shift 430, a driving mechanism for vertical shift 440, a fiber probe holder 450 and an electronic control unit (not shown).

The stage unit 420 is disposed on the substrate 410 and includes a nanoscale shift controller 422, a placing portion 424 and a hollow portion 426. The placing portion 424 is contained in the hollow portion 426 for supporting a glass slide (not shown). The nanoscale shift controller 422 connects to the placing portion 424 for adjusting the horizontal displacement of the placing portion 424 in fine tuning manner. In an embodiment, the nanoscale shift controller 422 is preferably a piezoelectric(PZT) actuator for controlling the horizontal displacement of the placing portion 424 down to nanoscale. The hollow portion 426 is a rectangular pit for accommodating a glass slide therein.

The driving mechanism for horizontal shift 430 is disposed on the substrate 410 for horizontally driving the stage unit 420 in X or Y direction displacement to nanoscale in fine tuning manner. The horizontal movement and displacement in this embodiment are accomplished by combination of the driving mechanism for horizontal shift 430 and the nanoscale shift controller 422 controlled by an electronic control unit. Other than the fine tuning horizontal movement and displacement, the coarse tuning down to 10 micrometer degree for the horizontal movement and displacement of the stage unit 420 in X or Y direction is achieved by two stepping motors, each of which is disposed at the bottom side and lateral side of the electric moving stage 400 respectively;

The driving mechanism for vertical shift 440 is disposed on the substrate 410 and has a cantilever arm extended from the left flank of the substrate 410 to the center of the stage unit 420 for supporting the fiber probe holder 450. Thus, the fiber probe holder 450 is suitably driven by the driving mechanism for vertical shift 440 to vertically move in Z direction displacement with precision up to micrometer degree. In the embodiment, the driving mechanism for vertical shift 440 is controlled by manual mode.

The fiber probe holder 450, which locates over the placing portion 424 of the stage unit 420, provides a holder aperture 452 for being inserted by the fiber probe (not shown).

In an embodiment, the stage unit 420 is preferably disposed on a microscope. The driving mechanism for horizontal shift 430 has a stepping motors (not shown) for horizontally driving the stage unit 420 in X or Y direction displacement by coarse tuning function. While the fine tuning function for horizontally driving the stage unit 420 in X or Y direction displacement is served by the nanoscale shift controller 422 via a double-axis PZT actuator. Namely, the horizontal displacement of the placing portion 424 of the glass slide is controlled by the nanoscale shift controller 422 while the horizontal displacement of the nanoscale shift controller 422 is controlled by the driving mechanism for horizontal shift 430. Thus, the cell specimen on the glass slide is able to freely moved during the operation of the microscope. The holder aperture 452 of the fiber probe holder 450 is centered in desired area of the microscopic field. By the electric moving stage 400, the target cells of interest is centered in a target area of the microscope field to align the fiber probe. A laser beam, triggered by a driving circuit, irradiates via the fiber probe and melts the EVA transfer membrane 140 to capture the target cells.

Figure 6:
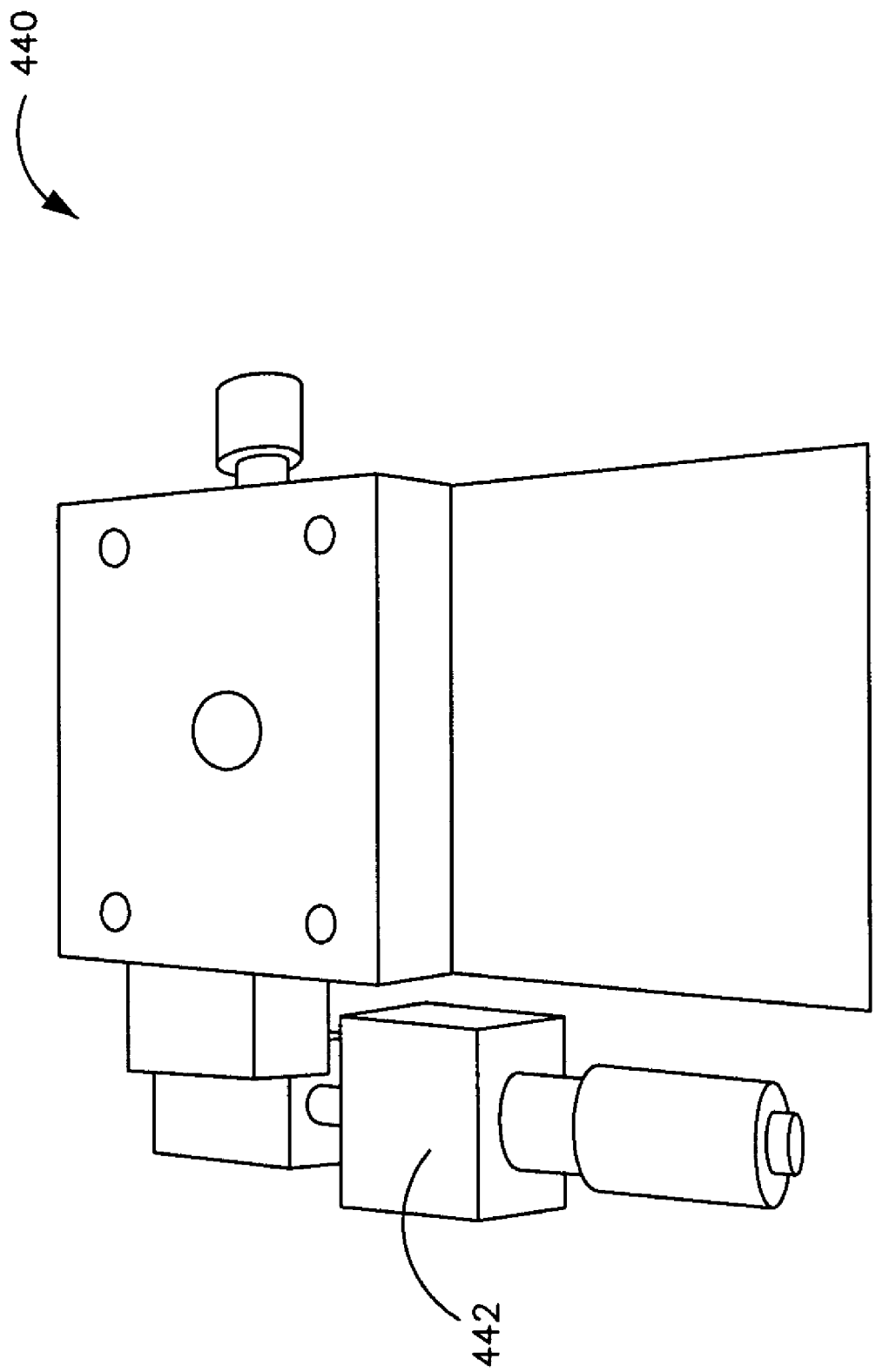
FIG. 6 is a schematic view showing a driving mechanism for vertical shift in an electric moving stage for a laser capture microdissection system of the present invention.

Refer to FIG. 5 and FIG. 6, the driving mechanism for vertical shift 440 includes a PZT actuator 441, which serves for fine tuning control of the vertical displacement of the holder aperture 452 of the fiber probe holder 450 in nanoscale. The driving mechanism for vertical shift 440 has a manual rotary shaft 442.

Figure 7:
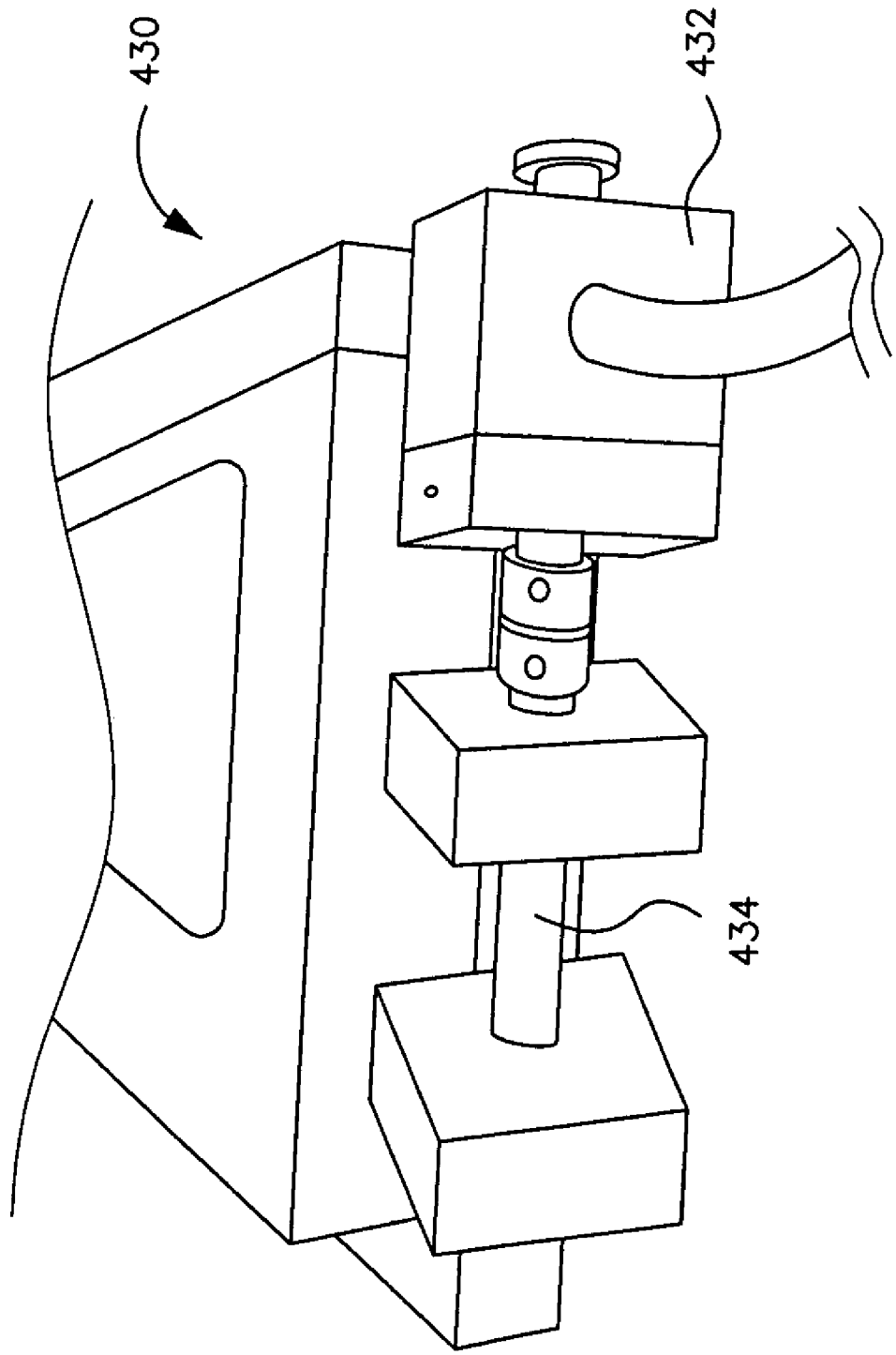
FIG. 7 is a schematic view showing a driving mechanism for horizontal shift in an electric moving stage for a laser capture microdissection system of the present invention.

Refer to FIG. 5 and FIG. 7, the driving mechanism for horizontal shift 430 includes a stepping motor 432 and a ball screw shaft 434. The movement and displacement of the stage unit 420 is motorized by ball screw shaft 434 driven by the stepping motor 432. In this embodiment, because the nanoscale shift controller 422 (the PZT actustor) is susceptible to tiny vibration with serious error, not only the high precision of the ball screw shaft 434 is adopted but also the material of the stage unit 420 is the cast iron processed by anodic treatment to assure the stable and smooth operation of the LCM system.

Figure 8:
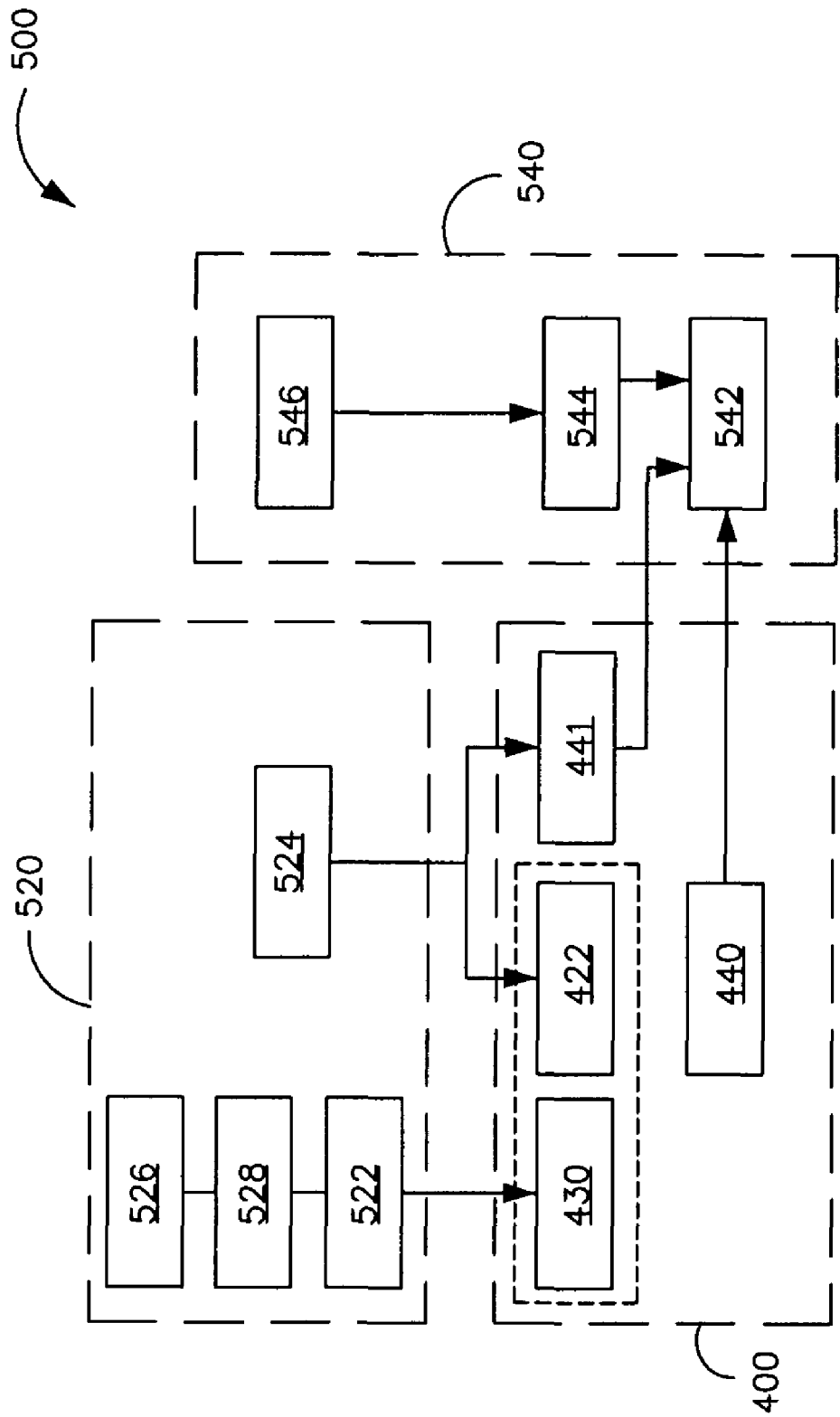
FIG. 8 is a block diagram showing a hardware configuration for a laser capture microdissection system of the present invention.

Refer to FIG. 8 for the block diagram showing a hardware configuration for a LCM system 500 of the present invention. The laser capture microdissection system 500 functionally includes an electronic control unit 520, an optical unit 540 and an electric moving stage 400. The electronic control unit 520 includes a stepping motor driver 522, a PZT actuator driver 524, a personal computer (PC) 526, and a interface card 528. The stepping motor driver 522 electrically connects to the driving mechanism for horizontal shift 430 of the electric moving stage 400. The PZT actuator driver 524 serves to drive the nanoscale shift controller 422, the PZT(XY) actuator of X and Y axes, and the PZT(Z) actuator 441 of Z axis of the driving mechanism for vertical shift 440. The back of the PZT actuator driver 524 contains a GPIB interface to connect with the PC 526. The optical unit 540 includes a laser illuminator 544, a fiber probe 542 and a laser diode driving circuit 546.

The activating duration for the laser diode illuminator 544 is controlled by the laser diode driving circuit 546 in range of 0 ms~9999 ms via current power supply of 0.3 ampere.

The fiber probe 542 has a coupling terminal and a probe terminal. The coupling terminal connects to the laser illuminator 544, and the probe terminal is inserted into the holder aperture 452 of the fiber probe holder 450 on the electric moving stage 400. The laser illuminator 544, which is a fabricated laser diode, is made of single mode fiber (SMF) in high power pigtail type.

The driving mechanism for horizontal shift 430, which has RS232 interface connector for connecting with computer in compatible manner, sends driving signal to the stepping motor 432 for driving the ball screw shaft 434 to horizontally move the stage unit 420 so that the center placing portion 424 in the stage unit 420 is enabled to move in X and Y directions as shown in FIG. 5.

The PZT(XY) actuator 422 has a fixed terminal and a movable terminal. The movable terminal is enabled to perform displacements in X and Y directions in relative range of 0~100 μm to response input voltage range of −10~150 V with displacement ratio in 625 nm/1.0 V.

Similarly, a movable terminal of the PZT(Z) actuator 441 is enabled to perform displacement in Z direction in relative range of 0~100 μm to response input voltage range of −10~150 V with displacement ratio in 406.25 nm/1.0 V;

The vertical movement in Z axis direction of the driving mechanism for vertical shift 440 is controlled by the manual rotary shaft 442 as shown in FIG. 5;

Refer to FIG. 5 through FIG. 8, the driving movements and controls for the fiber probe 542 and the stage unit 420 of the glass slide are recited as below.

Fiber Probe 542: The electric moving stage 400 with erected fiber probe 542 is already placed on a inverted microscope in this embodiment. In fine tuning mode, the PZT(Z) actuator 441 disposed on the driving mechanism for vertical shift 440 controls the Z axis displacement of fiber probe 542 via output driving voltage from the PZT actuator driver 524 in displacement ratio of 406.25 nm/1 V. In coarse tuning mode, the manual rotary shaft 442, which is on the driving mechanism for vertical shift 440, controls the Z axis displacement of fiber probe 542 to 0.02 mm with great precision. By combination of the PZT(Z) actuator 441 in fine tuning mode and the manual rotary shaft 442 in coarse tuning mode, the position and distance between the fiber probe 542 and the target object is precisely controlled.

Stage Unit 420: In coarse tuning mode, the stepping motor 432 controls the X and Y axes displacements of stage unit 420, wherein the stepping motor 432 is categorized into the permanent magnet (PM) type, the variable reluctance (VR) type and the hybrid (HB) type. In fine tuning mode, the PZT(XY) actuator 422 disposed on the stage unit 420 controls the X and Y axes displacements of the placing portion 424 of the glass slide so that the PZT actuator driver 524 supplies 1 V to shift the displacement of 625.25 nm. Because the target cell specimen is placed in the glass slide, by combination of the PZT(XY) actuator 422 in fine tuning mode and the stepping motor 432 in coarse tuning mode, the position and distance of the stage unit 420 is precisely operated to control the position of the target cell specimen in the microscopic field.

Because the stepping motor 432 is usually driven in open loop control, a built-in pulse signal generator in the stepping motor controller is required to generate pulse signal train to the stepping motor driver. Currently, many pulse signal generators (PSG) are available such as the 8051 PSG, the 8052 PSG of single chip 8-bit microprocessor and the 8255 interface card 528, which generates pulse signal train via PC programmable language.

In this embodiment, the fiber probe 542 is relatively confined in the microscopic field instead of following the movement of the stage unit 420 because the movement of fiber probe 542 is independent of the movement of electric moving stage 400. Then, the relative microscopic field position of the fiber probe 542, which is on the stage unit 420, is finished as long as the operation of the electronic control unit 520 and the electric moving stage 400 is completed. At this moment, by operating the optical unit 540, a laser beam, which is illuminated from the laser diode 544 activated by the laser diode driving circuit 546, focuses and melts the EVA transfer membrane via the outlet of the fiber probe 542 to finish the process of laser capture microdissection.

In concluding all the disclosure heretofore, the movement of the stage unit 420 and the movement of the fiber probe 542 in the present invention are separated and independent of each other. The fiber probe 542 is relatively confined in the microscopic field. Whereas, the stage unit 420 is relatively confined in planar two-dimensional movement of X and Y axes and is subjected by the electric moving stage 400. Expectantly, the overall speed and performance of the laser capture microdissection (LCM) system 500 is enable be significantly improved via the man-machine interface.

Figure 9:
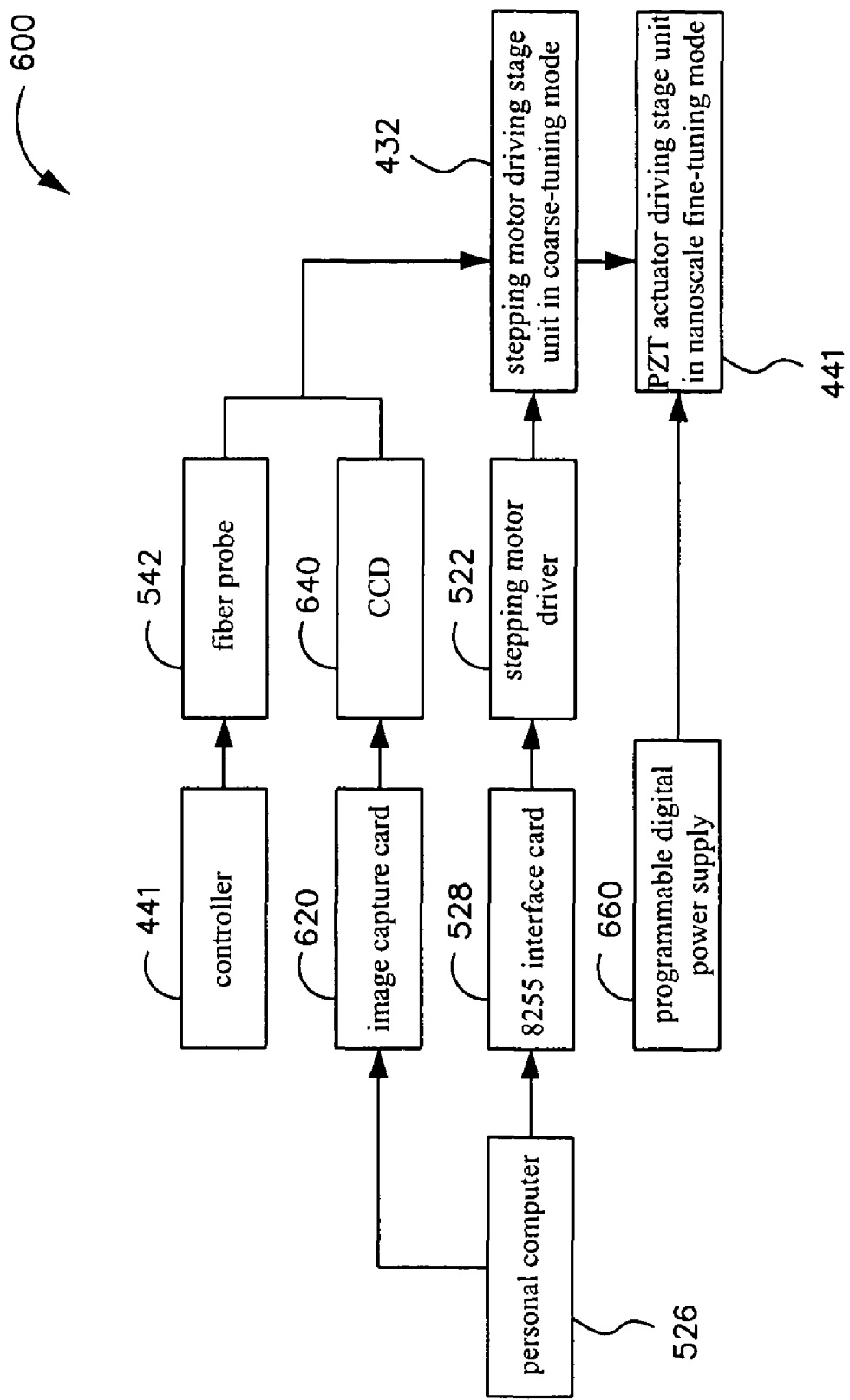
FIG. 9 is a block diagram showing a control function for a laser capture microdissection system of the present invention.

Practically, the laser capture speed of the laser capture microdissection (LCM) system 500 is considerably promoted by means of the application program in the stage unit 420. The performance improvements in reducing error, saving operation time and simplifying manipulation are substantially achieved via combination of man-machine interface and electric moving stage 400. Refer to FIG. 9 for the block diagram showing a control function for a laser capture microdissection system 600 of the present invention. The 8255 interface card 528 in this exemplary embodiment serves as the I/O interfaces for the stepping motor driver 522 and the PZT actuator 441 of driving mechanism for vertical shift 440. Besides, the control program for the 8255 interface card 528, which is compiled by the Visual Basic program language, covers definitions of I/O ports thereof, numbers of time clock for acceleration and deceleration of the stepping motors. The PC 526 serves as a console. Under the commands of the PC 526, the effective pulse signal train, which is generated from the 8255 interface card 528 and transmitted to the stepping motor driver 522 for being amplified therein, is used for driving the stepping motor 432 to control the movements and displacements of the stage unit 420 in both X and Y directions so that the coarse tuning displacement of the electric moving stage 400 is accomplished effectively.

In fine tuning mode, by means of nanoscale PZT (XY) actuator 441, which is energized by the programmable digital power supply 660, the horizontal movements and displacements of the glass slide in both X and Y directions is effectively controlled so the image observed by the charge coupled device (CCD) camera 640 is accomplished effectively under the microscopic field. The image capture card 620 captures the image in the CCD camera 640 and relays the image in the display monitor of the PC 526 for inspection to determine whether the glass slide in center target area of the microscopic field.

The foregoing description of the preferred embodiment of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like is not necessary limited the claim scope to a specific embodiment, and the reference to particularly preferred exemplary embodiments of the invention does not imply a limitation on the invention, and no such limitation is to be inferred. The invention is limited only by the spirit and scope of the appended claims. The abstract of the disclosure is provided to comply with the rules requiring an abstract, which will allow a searcher to quickly ascertain the subject matter of the technical disclosure of any patent issued from this disclosure. It is submitted with the understanding that it will not be used to interpret or limit the scope or meaning of the claims. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A laser capture microdissection system, comprising a shift control unit, an optical unit and an electronic control unit electrically connected to the shift control unit, the optical unit comprising:

a laser illuminator, electrically connected to the electronic control unit for switching a triggered time of the laser illuminator, wherein the triggered time is larger than 30 millisecond; and a fiber, coupled to the laser illuminator, and having a probe terminal fixed on the shift control unit, and an aperture of the probe terminal is smaller than 200 nanometer, wherein the shift control unit further comprises a first piezoelectric actuator, a second iezoelectric actuator and an adapted gasket, and the first piezoelectric actuator and the second piezoelectric actuator are combined by the adapted gasket.

2. The laser capture microdissection system of claim 1, further comprising a transfer membrane disposed under the probe terminal of the fiber, and a distance between the probe terminal and the transfer membrane is less than 1.3 micrometer.

3. The laser capture microdissection system of claim 1, wherein the first piezoelectric actuator has a first fixed end and a first moving end shifted with a first axis corresponding to the first fixed end; the second piezoelectric actuator has a second fixed end and a second moving end shifted with a second axis corresponding to the second fixed end; the second fixed end of the second piezoelectric actuator is fixed on the first moving end of the first piezoelectric actuator, and the probe terminal of the fiber is fixed on the second moving end of the second piezoelectric actuator.

4. The laser capture microdissection system of claim 3, wherein the shift control unit further comprises a shift stage for three axis, and the first fixed end of the first piezoelectric actuator is fixed on the shift stage for three axis.

5. The laser capture microdissection system of claim 1, wherein a surface of the probe terminal of the fiber is plated with a gold film or a silver film, whose thickness is 10 to 99 nanometer.

6. A laser capture microdissection system, comprising:
   a laser illuminator, having a triggered time larger than 30 millisecond;
   a fiber, having a probe terminal and a coupling terminal for being coupled to the laser illuminator; and
   an electric moving stage, comprising:
      a fiber probe holder, providing a holder aperture for being inserted by the probe terminal of the fiber;
      a driving mechanism for vertical shift, serving for driving the fiber probe holder to shift in microscale;
      a stage unit, including a nanoscale shift controller, a placing portion and a hollow portion, wherein the nano-scale shift controller connecting to the placing portion, and the placing portion locating under the holder aperture of the fiber probe holder;
      a driving mechanism for horizontal shift, serving for driving the stage unit to shift in microscale; and
      an electronic control unit, electrically connecting to the nanoscale shift controller of the stage unit and the driving mechanism for horizontal shift.

7. The laser capture microdissection system of claim 6, wherein said nanoscale shift controller of the stage unit is a piezoelectric actuator for controlling the displacement of the placing portion in nanoscale.

8. The laser capture microdissection system of claim 6, wherein said hollow portion of the stage unit is a rectangular pit for accommodating a glass slide to be supported by the placing portion.

9. The laser capture microdissection system of claim 6, wherein said driving mechanism for horizontal shift includes a stepping motor and a ball screw shaft so that the stage unit is motorized by the ball screw shaft driven by the stepping motor.

10. The laser capture microdissection system of claim 6, wherein said driving mechanism for vertical shift includes a piezoelectric actuator for controlling the displacement of the holder aperture of the fiber probe holder in nanoscale.

11. The laser capture microdissection system of claim 6, wherein said electronic control unit includes a stepping motor driver, a piezoelectric actuator driver and a PC, the stepping motor driver electrically connects to the driving mechanism for horizontal shift, and the piezoelectric actuator driver electrically connects to the nanoscale shift controller and driving mechanism for vertical shift.

12. The laser capture microdissection system of claim 6, wherein said driving mechanism for vertical shift has a manual rotary shaft.

13. An electric moving stage for a laser capture microdissection system, comprising:
   a substrate;
   a stage unit, which is disposed on the substrate, including a nanoscale shift controller, a placing portion and a hollow portion, wherein the nanoscale shift controller connecting to the placing portion, which is inside the hollow portion;
   a driving mechanism for horizontal shift, which is disposed on the substrate for driving the stage unit to shift in microscale;
   a driving mechanism for vertical shift is disposed on the substrate ;
   a fiber probe holder, which is driven by the driving mechanism for vertical shift to shift in microscale, which locates over the placing portion of the stage unit, providing a holder aperture; and
   an electronic control unit, electrically connecting to the nanoscale shift controller of the stage unit and the driving mechanism for horizontal shift.

14. The electric moving stage for the laser capture microdissection system of claim 13, wherein said nanoscale shift controller of the stage unit is a piezoelectric(piezoelectric) actuator for controlling the displacement of the placing portion in nanoscale.

15. The electric moving stage for the laser capture microdissection system of claim 13, wherein said hollow portion of the stage unit is a rectangular pit for accommodating a glass slide to be supported by the placing portion.

16. The electric moving stage for the laser capture microdissection system of claim 13, wherein said driving mechanism for horizontal shift includes a stepping motor and a ball screw shaft so that the stage unit is motorized by the ball screw shaft driven by the stepping motor.

17. The electric moving stage for the laser capture microdissection system of claim 13, wherein said driving mechanism for vertical shift includes a piezoelectric actuator for controlling the displacement of the holder aperture of the fiber probe holder in nanoscale.

18. The electric moving stage for the laser capture microdissection system of claim 13, wherein said electronic control unit includes a stepping motor driver, a piezoelectric actuator driver and a personal computer (PC), the stepping motor driver electrically connects to the driving mechanism for horizontal shift, and the piezoelectric actuator driver electrically connects to the nanoscale shift controller and the driving mechanism for vertical shift.

19. The electric moving stage for the laser capture microdissection system of claim 13, wherein said driving mechanism for vertical shift has a manual rotary shaft.

\* \* \* \* \*